United States Patent [19]

Witte et al.

[11] 4,020,257
[45] Apr. 26, 1977

[54] CATALYSTS

[75] Inventors: Josef Witte, Cologne; Günther Lehnert, Leverkusen, both of Germany

[73] Assignee: Bayer Aktiengesellschaft, Germany

[22] Filed: June 24, 1975

[21] Appl. No.: 589,935

Related U.S. Application Data

[62] Division of Ser. No. 523,022, Nov. 12, 1974, Pat. No. 3,966,637.

[30] Foreign Application Priority Data

Nov. 16, 1973 Germany .......................... 2357193

[52] U.S. Cl. ............................................... 526/143
[51] Int. Cl.$^2$ ..................... C08F 4/22; C08F 32/04
[58] Field of Search ..................... 260/93.1, 683 D; 526/143

[56] References Cited

UNITED STATES PATENTS 3,631,010  12/1971  Witte et al. ..................... 260/93.1
3,836,593  9/1974   Streck et al. ..................... 260/93.1

*Primary Examiner*—Edward J. Smith
*Attorney, Agent, or Firm*—Connolly and Hutz

[57] ABSTRACT

Catalysts obtained from
 A. a reaction product of 1 mol tungsten hexachloride with from 1 to 4 mols of a mixture of 2-chloroethanol and 2,2,2-trichloroethanol in a molar ratio of from 1 : 3 to 3 : 1; and
 B. from 1 to 20 mol, per mol of tungsten in component (A), of an organometallic aluminium for disproportionation and metathesis of olefin and for ring opening polymerization of cyclic olefins.

4 Claims, No Drawings

CATALYSTS

CROSS-REFERENCE TO RELATED APPLICATION

This application is a division of application Ser. No. 523,022 filed Nov. 12, 1974 now U.S. Pat. No. 3,966,637.

Catalysts obtained from tungsten salts and organic aluminium compounds are known. They are used inter alia for the disproportionation and for the metathesis of olefins and for the ring opening polymerisation of cyclic olefins. From German Offenlegungsschrift No. 1,770,491 it is known to increase the activity of these catalysts by the addition of 2-haloalcohols, e.g. 2-chloroethanol, and thus achieve decisive improvements in their technical utility. The reaction products of $WCl_6$ and 2-chloroethanol, for example, are soluble in inert organic solvents, (e.g. toluene), and stable in this solution, whereas $WCl_6$ itself is only sparingly soluble and its reaction products with alcohols which are free from halogen, e.g. ethanol, although soluble, are not stable since they decompose after a short time with precipitation of tungsten oxychlorides.

Reaction products of tungsten compounds with 2,2,2-trichloroethanol yield catalysts of insufficient activity.

This invention relates to catalysts obtained from

A. a reaction product of 1 mol tungsten hexachloride and from 1 to 4 mols of a mixture of 2-chloroethanol and 2,2,2-trichloroethanol in a molar ratio of from 1 : 3 to 3 : 1; and B. from 1 to 20 mol, per mol of tungsten in component (A), of an organometallic aluminium compound.

Reaction products (A) may be prepared by reacting tungsten hexachloride, in an inert solvent, with the mixture of chloroethanol and trichloroethanol. The reaction is preferably carried out at temperatures of from 10° to 30° C and preferably with the exclusion of air and moisture. Suitable solvents are i.a. aromatic hydrocarbons, chlorinated aromatic hydrocarbons and chlorinated aliphatic hydrocarbons, for example benzene, toluene, xylene, chlorobenzene, trichloromethane and dichloromethane. Toluene and dichloromethane are preferred.

The mixture of chloroethanol and trichloroethanol is used in a quantity of from 1 to 4 mol and preferably from 1.5 to 2.5 mol per mol tungsten hexachloride. The molar ratio of chloroethanol to trichloroethanol is from 1 : 3 to 3 : 1, preferably about 1 : 1. The quantities of reactants and solvents used are generally calculated to produce a solution of reaction product containing from 0.05 to 0.5 mol tungsten per liter.

The organometallic aluminium compounds which constitute component (B) of the catalyst are preferably compounds corresponding to the following general formula:

(I)

wherein $R_1$ represents an alkyl group with 1 – 12 C-atoms, $R_2$ represents an alkyl group with 1 – 12 C-atoms, chlorine, bromine or an alkoxy group with 1 – 12 C-atoms; $R_3$ represents an alkyl group with 1 – 12 C-atoms, chlorine, bromine or an alkoxy group with 1 – 12 C-atoms. The following are examples of such compounds: aluminium trialkyls such as aluminium trimethyl, aluminium triethyl or aluminium triisobutyl; aluminium alkyl halides, such as diethyl aluminium chloride, diisobutyl aluminium chloride, diethyl aluminium bromide or aluminium ethyl dichloride; and aluminium alkoxy alkyls, such as ethoxy aluminium diethyl. Mixtures of such compounds are also suitable, e.g. so-called "aluminium sesquichloride", $Al_2(C_2H_5)_3Cl_3$. Dialkyl aluminium chlorides are particularly preferred, e.g. diethyl aluminium chloride.

The organometallic aluminium compounds which constitute component (B) of the catalysts according to the invention are used in quantities of from 1 to 20 mol, preferably from 2 to 8 mol per mol tungsten in component (A).

These catalysts have a much longer life than the known catalysts. The active catalyst may maintain its activity for up to 17 hours at 0° C whereas known catalysts are inactive after only 1 or 2 hours at 0° C.

The catalysts according to the invention may be used for the disproportionation and for the metathesis of olefins and for the ring opening polymerisation of cyclic olefins. All these reactions can be carried out with or without inert organic solvents present.

The catalysts according to the invention can generally be used as follows:

1. the catalyst components are added in the sequence (A) - (B) or (B) - (A) or simultaneously to a solution, in an inert solvent, of the olefins or cycloolefins which are to be reacted, or 2. the active catalyst is prepared by mixing components (A) and (B) in an inert organic solvent and this preformed catalyst may then be contacted with the olefins or cycloolefins.

Method (1) is preferred.

The procedure employed for the metathesis of olefins and for the ring opening polymerisation are virtually identical. The procedure is generally as follows: component (A), optionally in the form of a solution in an inert organic solvent, is added to an approximately 5 to 50, preferably 15 to 30% by weight, solution of the olefins or cycloolefins in an inert organic solvent in a quantity corresponding to from 0.05 to 10, preferably from 0.1 to 1.0 mMol tungsten per 100 g of olefin or cycloolefin. The mixture is then activated by the addition of component (B) and the reaction is carried out at a temperature of from −60° to 60° C, preferably from −25° to 25° C. The whole process is carried out with the exclusion of oxygen and water, in most cases under an inert gas atmosphere, such as nitrogen. Suitable solvents for the process are, in particular, aliphatic hydrocarbons, such as pentane, hexane or isooctane, cycloaliphatic hydrocarbons, such as cyclopentane or cyclohexane, aromatic hydrocarbons, such as benzene, toluene or xylene and chlorinated hydrocarbons, such as methylene chloride, chloroform or chlorobenzene. Toluene and methylene chloride are preferred.

The above sequence for combining the catalyst components and the reactants is preferred but not essential. Any other sequence may be employed.

If open chain olefines are present in the reaction mixture, the substituents on the double bond are exchanged so that an olefine mixture is produced.

The reaction is illustrated by the following reaction scheme:

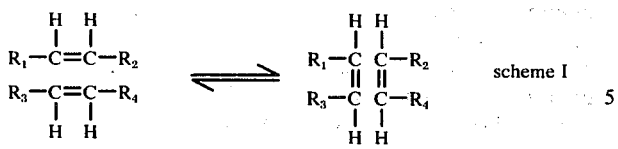

scheme I

Groups $R_1$ to $R_4$ in this scheme preferably represent $C_1$–$C_{10}$ alkyl groups. As may be seen from the reaction scheme, at least one of the groups $R_1$ to $R_4$ must be different from the others so that the exchange of groups $R_1$ to $R_4$ leads to reaction products which are different from the olefin originally present. A single olefin may therefore be processed if its two groups $R_1$ and $R_2$ are different from each other. In this way, pent-2-ene, for example, yields a mixture of but-2-ene (25%), pent-2-ene (50%) and hex-3-ene (25%).

The reaction may also be carried out with two or more olefins simultaneously. In that case, the various groups R are interchanged until an equilibrium state is reached.

After termination of the reaction, the catalyst can be inactivated by the addition of alcohols, carboxylic acids and/or amines. The reaction products can be separated by fractional distillation.

If a cycloolefin is subjected to this procedure a polyalkenamer is obtained, as indicated in the scheme II

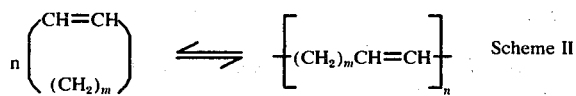

Scheme II wherein $n$ = an integer; and $m$ = 2, 3, or from 5 to 10.

Particularly suitable cycloolefines are the monocyclic monoolefines with 4, 5 or from 7 to 12 carbon atoms in the ring, e.g. cyclobutene, cyclopentene, cyclooctene or cyclododecene. Polymerisation of these compounds occurs as soon as the catalyst components have been combined and is recognised i.a. by a distinct increase in the viscosity of the polymerisation solution. Polymerisation is completed after from 1 to 6 hours, 80 to 90% conversions are obtained and no gel formation occurs. In addition to homo- and copolymerisation of monocyclic monoolefins, similarly copolymerisation with di- or polycyclic diolefins, e.g. norbornadiene is possible. Higher molecular weights are then obtained by the branching of the macromolecules. Alternatively, open chain olefins, such as but-1-ene, but-2-ene or pent-2-ene, may be added, in which case the molecular weights obtained are lower.

In this procedure the catalyst can also be inactivated by adding alcohols, carboxylic acids and/or amines when the desired degree of conversion has been obtained. In most cases, it is necessary to stabilise the resulting polymer against atmospheric oxygen by means of antioxidants, such as phenyl-β-naphthylamine, 2,5-di-tert.-butyl-4-methyl-phenol or 2,2'-dihydroxy-3,3'-di-tert.-butyl-5,5-dimethyl-diphenyl-methane. The polymer may be isolated from this pretreated solution by means of non-solvents, such as methanol, ethanol, isopropanol or acetone, or by steam distillation. The process may be carried out either batch-wise or continuously. The polymers are generally rubber-like substances or thermoplastic products.

EXAMPLES

Preparation of Catalyst Component (A)

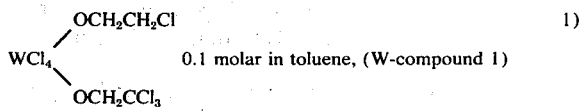

1) 0.1 molar in toluene, (W-compound 1)

200 ml anhydrous toluene and 11.9 g $WCl_6$ (30 mMol) are introduced into a stirrer vessel with the exclusion of oxygen and mixture.

A mixture of 92 ml toluene, 2 ml chlorethanol and 2.9 ml trichloroethanol is added dropwise at room temperature with vigorous stirring over a period of 60 minutes. The initial blue colour of the $WCl_6$ solution in toluene changes to brown in the course of the reaction, and $WCl_6$ goes into solution completely.

2. $WCl_4(OCH_2\text{-}CH_2Cl)_2$ 0.1 molar in toluene, (W-compound 2)

11.9 g $WCl_6$ are reacted with 4.0 ml 2-chloroethanol in a total of 293 ml toluene in the manner described under part (1) above. A dark brown solution of the tungsten compound in toluene is again obtained.

EXAMPLE 1

Solution Polymerisation of Cyclopentene

General Method of Procedure 1300 ml anhydrous toluene and 200 g cyclopentene are introduced into a stirrer vessel with the exclusion of oxygen and moisture. The mixture is cooled to −15° C under a protective gas atmosphere of dry nitrogen. 0.6 mMol tunsten compound is then added in the form of a 0.1 molar solution in toluene. $Al(C_2H_5)_2Cl$ is then added as a 1.0 molar solution in toluene in the optimum quantity for the given tungsten compound. Suitable external cooling is applied to ensure that the reaction temperature gradually rises from −15° to −5° C in the course of 3 hours. Polymerisation is then stopped by the addition of 5 ml ethanol. The polymer is stabilised with 1 g 2,6-di-t.-butyl-4-methyl phenol, precipitated from the toluene solution with ethanol and dried under vacuum at 50° C.

The polymerisation conditions and experimental results are summarised in Table 1 below. Experiments I and II were carried out with the catalyst system according to the invention and experiment III is a comparison experiment.

Table 1

| Experiment | | I | II | III |
|---|---|---|---|---|
| Toluene | ml | 1300 | 1300 | 1300 |
| Cyclopentene | g | 200 | 200 | 200 |
| Temperature | ° C | −15 | −15 | −15 |
| W-compound 1 | mMol | 0.6 | 0.3 | — |
| W-compound 2 | mMol | — | — | 0.6 |
| $Al(C_2H_5)_2Cl$ | mMol | 3.0 | 2.0 | 1.8 |
| Polymerisation temperature | ° C | −15/−5 | −15/−5 | −15/−5 |
| Polymerisation time | h | 3 | 3 | 3 |
| Conversion | % | 80 | 79 | 79 |
| [η] toluene 25° C | dl/g | 2.1 | 2.8 | 2.75 |
| trans double bond | % | 80.3 | 79.5 | 80.0 |

When the same quantity of catalyst is used in each case, polymers with a lower molecular weight are obtained by the process according to the invention (compare experiment I and experiment III). Only half the catalyst concentration is therefore required to produce polymers with a similar molecular weight (compare experiment II and experiment III).

The advantages of the catalyst according to the invention are its greater economic efficiency and the reduced contamination of the effluent water with catalyst residues.

EXAMPLE 2

The life-time of the catalyst system using W-compound 1 according to the invention was determined by adding a fresh quantity of monomer (experiments I to V). Experiments VI to IX are comparison experiments using W-compound 2.

The experimental conditions and results are summarised in Table 2.

Table 2

| Experiment | I | II | III | IV | V | VI | VII | VIII | IX |
|---|---|---|---|---|---|---|---|---|---|
| | | | Experiments to determine the catalyst life at 0° C | | | | | | |
| Toluene | 1300 ml | 1300 ml | 1300 ml | 1300 ml | 1300 ml | 1300 ml | 1300 ml | 1300 ml | 1300 ml |
| Cyclopentene | 200 g | 100 g | 100 g | 100 g | 100 g | 200 g | 100 g | 100 g | 100 g |
| Temperature ° C | 0 | 0 | 0 | 0 | 0 | 0 | 0 | 0 | 0 |
| (Δ) W-compound 1, mMol | 0.6 | 0.6 | 0.6 | 0.6 | 0.6 | — | — | — | — |
| (O) W-compound 2, mMol | — | — | — | — | — | 0.6 | 0.6 | 0.6 | 0.6 |
| Al(C$_2$H$_5$)$_2$Cl mMol | 1.8 | 1.8 | 1.8 | 1.8 | 1.8 | 1.8 | 1.8 | 1.8 | 1.8 |
| Addition of 100 g of cyclopentene after | — | 2 h | 3 h | 4 h | 17 h | — | 1.5 h | 3 h | 4 h |
| 6 h conversion % | 77 | 80 | 78.5 | 79 | 79(+) | 72 | 43 | 29 | 29 |
| [η] dl/g toluene 25° C | 2.1 | 2.1 | 2.0 | 2.0 | 2.0 | 2.5 | 2.1 | 1.7 | 1.7 |

Legend to Table 2:
(Δ) W-compound 1:

(O) W-compound 2: WCl$_4$—(OCH$_2$—CH$_2$Cl)$_2$
(+) conversion after a total operating time of 20 hours Table 3

| Experiment | | I | II |
|---|---|---|---|
| Chlorobenzene | ml | 50 | 50 |
| cis-pent-2-ene | g | 10 | 10 |
| Temp. ° C | | 0 | 0 |
| W-compound 1, mMol | | 1.0 | — |
| W-compound 2, mMol | | — | 1.0 |
| Al(C$_2$H$_5$)$_2$Cl mMol | | 2.0 | 2.0 |
| Composition of the olefines (+) | | | |
| after 4 minutes but-2-ene | | 14% | — |
| pent-2-ene | | 72% | — |
| hex-3-ene | | 14% | — |
| after 10 minutes but-2-ene | | 25% | 7% |
| pent-2-ene | | 50% | 86% |
| hex-3-ene | | 25% | 7% |
| after 60 minutes but-2-ene | | — | 7.5% |
| pent-2-ene | | — | 85% |
| hex-3-ene | | — | 7.5% |

(+) mol % determined by gas-chromatography.

Experiments I – V show that the catalyst based on W-compound 1 has a life of at least 17 hours at 0° C. Monomer added after 17 hours is polymerised to the same final percentage conversion (experiment V) as in experiment 1.

The catalyst based on W-compound 2 (experiments VI – IX), on the other hand, has a life of less than 1.5 hours at 0° C. As may be seen from a comparison of experiments VI and VII, the percent conversion in 6 hours drops from 72% to 43% when the second monomer batch is added after only 1.5 hours.

These experiments demonstrate very clearly the substantially longer life of the catalyst system according to the invention.

Its advantages are particularly important in continuous processes, in which the residence time of the components in the polymerisation zone must be expected to vary over a wide range.

EXAMPLE 3

Olefine Metathesis

General Method of Procedure

A mixture of from 20 to 50% olefine and from 80 to 50% solvent is introduced into a stirrer vessel, with the exclusion of oxygen and water, and is cooled to 0° C. The tungsten compound is then added, followed by the organic aluminium compound. After the desired reaction time, the catalyst is destroyed by the addition of alcohol.

Table 3 below shows the experimental conditions and results of the metathesis of cis-pent-2-ene. Experiment 1 was carried out using the catalyst system according to the invention (W-compound 1) and experiment II is a comparison experiment.

In experiment I, the maximum possible percentage conversion is obtained after only 10 minutes whereas in comparison experiment II only 30% of the final conversion is obtained after 60 minutes.

We claim:
1. A process for the ring opening polymerization of monocyclic monoolefins having 4, 5 or from 7 to 12 carbon atoms in the ring, said process comprising contacting a 5 to 50% by weight solution of at least one of said monocyclic monoolefins in an inert organic solvent at −60° to 60° C. with a catalyst composition comprising:
A. a reaction product of 1 mol tungsten hexachloride with from 1 to 4 mols of a mixture of 2-chloroethanol and 2,2,2-trichloroethanol in a molar ratio of from 1:3 to 3:1 and
B. from 1 to 20 mol, per mol of tungsten in component (A), of an organometallic aluminum compound, said catalyst composition being employed in a quantity supplying from 0.05 to 10 mmol tungsten per 100 g. of said olefin.

2. The process of claim 1 wherein component (A) is added to the olefin solution, subsequently component (B) is added to said solution and the whole process is carried out substantially in the absence of air and moisture.

3. The process of claim 1 in which said olefin solution is 15 to 30% by weight, the quantity of tungsten in component (A) supplies from 0.1 to 1.0 mMol tungsten per 100 g. olefin and the reaction is carried out at a temperature of from −25° to 25° C.

4. The process of claim 1 wherein said contacted olefin is cyclopentene.

* * * * *